United States Patent
Jansen et al.

(10) Patent No.: US 6,290,965 B1
(45) Date of Patent: Sep. 18, 2001

(54) DNA ENCODING HUMAN PAPILLOMAVIRUS TYPE 6A

(75) Inventors: Kathrin U. Jansen, Fort Washington; Kathryn J. Hofmann, Collegeville, both of PA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/521,526

(22) Filed: Mar. 8, 2000

Related U.S. Application Data

(63) Continuation of application No. 08/983,527, filed on Jul. 31, 1997, now abandoned, which is a continuation of application No. 08/310,468, filed on Sep. 22, 1994, now abandoned.

(51) Int. Cl.$^7$ .............................. A61K 39/12; C12N 15/00
(52) U.S. Cl. .................................. 424/199.1; 424/204.1; 424/186.1; 435/320.1; 435/235.1; 435/239; 435/325; 435/91.1; 435/91.33; 514/44; 536/23.72; 536/23.1
(58) Field of Search .............................. 424/704.1, 199.1, 424/186.1; 435/91.1, 91.33, 235.1, 325, 239, 320.1; 514/44; 536/23.72, 23.1

(56) References Cited

PUBLICATIONS

Bercovich et al., "Presence and integration of human papillomarvirus type 6 in a tonsillar carcinoma" Journal of General Virology, vol. 72, pp. 2569–2572, 1991.

Boshart et al., "Human papillomarvirus in Buschke–Lowenstein tomors: Physical state of the DNA and identification of a tandem duplication in the noncoding region of a human papillomavirus 6 subtype" Journal of Virology vol. 58 Issue 3 pp. 963–966, 1986.

Brown et al., "Analysis of human papillomavirus types in exophytic condylomata by hybrid capture and Southern blot techniques" Journal of Clinical Microbiology, vol. 31, Issue 10 pp.2667–2673, 1993.

De Villiers et al., "Molecular cloning of viral DNA from human genital warts" Journal of Virology, vol. 40, Issue 3, pp. 932–935, 1981.

Di Lorenzo et al., "Human papillomavirus type 6a in the lung carcinoma of a patient with recurrent laryngeal papillomavirus is characterized by a partial duplication" Journal of Virology, vol. 73, pp. 423–428, 1992.

Sasagawa et al., "Synthesis and assembly of virus–like particles in human papillomavirus type 6 and type 16 in fission yeast Schizosaccharomyces Pombe" Virology, vol. 206, pp. 126–135, Jan. 1995.

*Primary Examiner*—Ali R. Salimi
(74) *Attorney, Agent, or Firm*—Joanne M. Giesser; Jack L. Tribble

(57) ABSTRACT

The present invention is directed to DNA molecules encoding purified human papillomavirus type 6a and compounds derived therefrom.

12 Claims, 7 Drawing Sheets

1                    [E6→
GTTAATAACAATCTTGGTTTTAAAAAAATAGGAGGGACCGAAAACGGTTCAACCGAAAACGGTTGTATATAAACCAGCCCTAAAATTTAGCAAACGAGCCA

101
TTATGGAAAGTGCAAATGCCTCCACGTCTGCAACGACCATAGACCACTTGTGCAAGACGTTTAATCTATCTATGCATACGTTGCAAATTAATTGTGTGTT

201
TTGCAAGAATGCACTGACCACTGCAGAGATTTATTCATATGCATATAAACAGCTAAAGGTCCTGTTTCGAGGCGGCTATCCATATGCAGCCTGCGCGTGC
                A                                        C
301
TGCCTAGAATTTCATGGAAAAATCAACCAATATAGACACTTTGATTATGCTGGATATGCAACAACTGTTGAAGAAGAAACTAAACAAGACATTTTAGACG
                A                                       A                            C
401                         [E7→
TGCTAATTCGGTGCTACCTGTGTCACAAACCGCTGTGTGAAGTAGAAAAGGTAAAACATATACTAACCAAGCGCGGTTTATAAAGCTAAATTGTACGTG
                                                                                           C
501                              ←E6]
GAACGGTCGCTGCCTACACTGCTGGACAACATGCATGGAAGACATGTTACCCTAAAGGATATTGTATTAGACCTGCAACCTCCAGACCCTGTAGGGTTAC

601
ATTGCTATGAGCAATTAGTAGACAGCTCAGAAGATGAGGTGGACGAAGTGGACGGACAAGATTCACAACCTTTAAAACAACATTTCCAAATAGTGACCTG

701         [E1→
TTGCTGTGGATGTGACAGCAACGTTCGACTGGTTGTGCAGTGTACAGAAACAGACATCAGAGAAGTGCAACAGCTTCTGTTGGGAACACTAGACATAGTG
                                                                                                 A
801              ←E7]
TGTCCCATCTGCGCACCGAAGACATAACAACGATGGCGGACCATTCAGGTACAGAAAATGAGGGGTCTGGGTGTACAGGATGGTTTATGGTAGAAGCTAT
                                C
901
AGTGCAACACCCAACAGGTACACAAATATCAGACGATGAGGATGAGGAGGTGGAGGACAGTGGGTATGACATGGTGGACTTTATTGATGACAGCAATATT

1001
ACACACAATTCCTTGGAAGCACAGGCATTGTTTAACAGGCAGGAGGCGGACACCCATTATGCGACTGTGCAGGACCTAAAACGAAAGTATTTAGGTAGTC
             AC
1101
CATATGTTAGTCCTATAAACACTATAGCCGAGGCAGTGGAAAGTGAAATAAGTCCACCATTGGACGCCATTAAACTTACAAGACAGCCAAAAAAGGTAAA

1201
GCGACGGCTGTTTCAAACCAGGGAACTAACGGACAGTGGATATGGCTATTCTGAAGTGGAAGCTGGAACGGGAACGCAGGTAGAGAAACATGGCGTCCCG
                                                                                                 A

FIG.1A

1301
GAAAATGGGGGACATGGTCAGGAAAAGGACACAGGAAGGGACATAGAGGGGGAGGAACATACAGAGGCGGAAGCGCCCACAAACAGTGTACGGGAGCATG

1401
CAGGCACAGCAGGAATATTGGAATTGCTAAAATGTAAAGATTTACGGGCAGCATTACTTGGTAAGTTTAAAGAATGCTTTGGGCTGTCTTTTATTGATTT
                T                                                                                A
1501
AATTAGGCCATTTAAAACTGATAAAACAACATGTGCAGACTGGGTGGTAGCAGGATTTGGTATACATCATAGCATATCAGAGGCATTTCAAAAATTAATT
                 TT  T                 G
1601
GAGCCATTAAGTTTATATGCACATATACAATGGCTAACAAATGCATGGGGAATGGTATTGTTAGTATTAGTAAGATTTAAAGTAAATAAAAGTACAAGTA
                                                                              T
1701
CCGTTGCACGTACACTTGCAACGCTATTAAATATACCTGACAATCAAATGTTAATAGAGCCACCAAAAATACAAAGTGGTGTTGCAGCCCTGTATTGGTT
                    A C
1801
TCCTACAGGTATATCAAATGCCAGTACAGTTATAGGGGAAGCACCAGAATGGATAACACGCCAAACTGTTATTGAACATGGGTTGGCAGACAGTCAGTTT
                                                                A               C
1901
AAATTAACAGAAATGGTGCAGTGGGCATATGATAATGACATATGCGAGGAGAGTGAAATTGCATTTGAATATGCACAAAGGGGAGATTTTGATTCTAATG
                            G
2001
CACGAGCATTTTTTAAATAGCAATATGCAGGCAAAATATGTGAAAGATTGTGCAACTATGTGTAGACATTATAAACATGCAGAAATGAGGAAGATGTCTAT

2101
AAAACAATGGATAAAACATAGGGGTTCTAAAATAGAAGGCACAGGAAATTGGAAACCAATTGTACAATTCCTACGACATCAAAATATAGAATTTATTCCA
                                                                          C   T
2201
TTTTTAAGTAAATTTAAATTATGGCTGCACGGTACGCCAAAAAAAAACTGCATAGCCATAGTAGGCCCTCCAGATACTGGGAAATCGTACTTTTGTATGA
     C
2301
GTTTAATAAGCTTTTTACGAGGTACAGTTATTAGTCATGTAAATTCCAGCAGCCATTTTTGGTTGCAACCGTTAGTAGATGCTAAGGTAGCATTGTTAGA
          C
2401
TGATGCAACACAGCCATGTTGGATATATATGGATACATATATGAGAAATTTGTTAGATGGTAATCCTATGAGTATTGACAGAAAGCATAAAGCATTGACA

2501
TTAATTAAATGTCCACCTCTGCTAGTAACGTCCAACATAGATATTACTAAAGAAGAGAAATATAAGTATTTACATACTAGAGTAACAACATTTACATTTC
                                                                     T

FIG.1B

```
2601                                                                                     [E2→
CAAATCCATTCCCTTTTGACAGAAATGGGAATGCAGTGTATGAACTGTCAAATGCAAACTGGAAATGTTTTTTTGAAAGACTGTCCTCAAGCCTAGACAT
                                             A

2701                                                                     ←E1]
TCAGGATTCAGAGGACGAGGAACATGGAAGCAATAGCCAAGCGTTTAGATGCCTGCCAGGAACAGTTGTTAGAACTTTATGAAGAAAACAGTACTGACCT
            T

2801
AAACAAACATGTATTGCATTGGAAATGCATGAGACATGAAAGTGTATTATTATATAAAGCAAAACAAATGGGCCTAAGCCCACATAGGAATGCAAGTAGTG
C

2901
CCACCATTAAAGGTGTCCGAAGCAAAAGGACATAATGCCATTGAAATGCAAATGCATTTAGAATCATTATTAAAGACTGAGTATAGTATGGAACCGTGGA
                                                                                       G

3001
CATTACAAGAAACAAGTTATGAAATGTGGCAAACACCACCTAAACCCTGTTTTAAAAAACGGGGCAAAACTGTAGAAGTTAAATTTGATGGCTGTGCAAA

3101
CAATACAATGGATTATGTGGTATGGACAGATGTGTATGTGCAGGACACTGACTCCTGGGTAAAGGTGCATAGTATGGTAGATGCTAAGGGTATATATTAC
                                             A       A
3201                    [E4→
ACATGTGGACAATTTAAAACATATTATGTAAACTTTGTAAAAGAGGCAGAAAAGTATGGGAGCACCAAACAATGGGAAGTATGTTATGGCAGCACAGTTA
                                                                T

3301
TATGTTCTCCTGCATCTGTATCTAGCACTACACAAGAAGTATCCATTCCTGAATCTACTACATACACCCCCGCACAGACCTCCACCCCTGTGTCCTCAAG
                                                                                              T

3401
CACCCAGGAAGACCCAGTGCAAACGCCGCCTAGAAAACCAGCACGAGGAGTCCAACAGTCACCTTGCAACGCCTTGTGTCTGGCCCACATTGCACCCGTG
         A                     G                    C
3501                                                                         ←E4]
GACAGTGGAAACCACAACCTCATCACTAACAATCACGACCAGCACCAAAGAAGGAACAACAGTAACAGTTCAGCTACGCCTATAGTGCAATTTCAAGGTG
                                                               C

3601
AATCTAATTGTTTAAAGTGTTTTAGATATAGGCTAAATGACAAACACAGACATTTATTTGATTTAATATCATCAACGTGGCACTGGGCCTCCCCAAAGCC
           C                         G                                                  T
3701
ACCACATAAACATGCCATTGTAACTGTAACATATCATAGTGAGGAACAAAGGCAACAGTTTTTAAATGTTGTAAAAATACCACCTACTATTAGGCACAAA
                    G                               G            C   C   C
3801            ←E2]                                                                [E5→
CTGGGGTTTATGTCACTGCACCTATTGTAATTTGTATATATGTAAATGTGTAAATATATGGTATTGCTGTAATACAACTGTACATGTATGGAAGTGGTAC
        A                                                                                          G
```

FIG.1C

3901
CTGTACAAATAGCTGCAGGAACAACCAGCACATTAATACTGCCTGTTATAATTGCATTTGTTGTATGTTTTGTTAGCATCATACTTATTGTATGGATATC
                            C

4001
TGACTTTATTGTGTACACATCTGTGCTAGTACTAACACTGCTTTTATACTTACTATTGTGGCTGCTATTAACAACCCCCTTGCAATTTTTCCTACTAACT
       G                                 T                                      -[E5]
4101
CTACTTGTGTGTTACTGTCCCGCATTGTATATACACCACTACATTGTTAACACACAGCAATGATGCTAACATGTCAATTTAATGATGGAGATACATGGCT
                T      T       C                                                                   C

4201
GGGTTTGTGGTTGTTATGTGCCTTTATTGTAGGGGTGTTGGGGTTATTATTAATGCACTATAGAGCTGTACAAGGCGATAAACACACCAAATGTAACAAG
                  A                G                          G                                  G
                                                                                    [L2→
4301
TGTAAACAAACACACCTGTAATGCTGATTATGTAACTATGCATCATGATACTGCTGGTGATTATATATATATGAATTAGAGTAAAACTTTTTTTATATTTG
         A    A              T AC    A                                              C G

4401
TAACAGTGTATGTTTTGTATACCATGGCACATAGTAGGGCCCGACGACGCAAGCGTGCCTCAGCTACACAGCTATATCAAACATGTAAACTTACTGGAAC
         C                                                                                         C

4501
ATGCCCCCCAGATGTAATTCCTAAGGTGGAGCACAACACCATTGCAGATCAAATATTAAAATGGGGAAGTTTGGGGGTTTTTTTTGGAGGGTTGGGTATA
                                                                         G

4601
GGCACCCGTTCCGGCACTGGGGGTCGTACTGGCTATGTTCCCTTAGGAACTTCTGCAAAACCTTCTATTACTAGTGGGCCTATGGCTCGTCCTCCTGTGG
         G                                    CA

4701
TGCTGGAGCCTGTGGCCCCTTCGGATCCATCCATTGTGTCTTTAATTGAAGAATCAGCAATCATTAACGCAGGGGCGCCTGAAATTGTGCCCCCTGCACA
                    T                      G

4801
CCGTGGGTTTACAATTACATCCTCTGAAACAACTACCCCTGCAATATTGGATGTATCAGTTACTAGTCATACTACTACTAGTATATTTAGAAATCCTGTC
                                                                                          C

4901
TTTACAGAACCTTCTGTAACACAACCCCAACCACCCGTGGAGGCTAATGGACATATATTAATTTCTGCACCCACTATAACGTCACACCCTATAGAGGAAA
                                                                                       G

5001
TTCCTTTAGATACTTTTGTGATATCCTCTAGTGATAGCGGTCCTACATCCAGTACCCCTGTTCCTGGTACTGCACCTAGGCCTCGTGTGGGCCTATATAG
               G    A                                                                  C

5101
TCGTGCATTGCACCAGGTGCAGGTTACAGACCCTGCATTTCTTTCCACTCCTCAACGCTTAATTACATATGATAACCCTGTATATGAAGGGAGGATGTT

FIG.1D

5201
AGTGTACAATTTAGTCATGATTCTATACACAATGCACCTGATGAGGCTTTTATGGACATAATTCGTTTGCACAGACCTGCTATTGCGTCCCGACGTGGCC
                                                                            C

5301
TTCTGCCGTACAGTCGCATTGGACAACGGGGGTCTATGCACACTCGCAGCCGAAAGCACATAGGGGCCCGGCATTCATTATTTTTATGATATTTCACCTAT

5401
TGCACAAGCTGCAGAAGAAATAGAAATGCACCCTCTTGTGGCTGCACAGGATGATACATTTGATATTTATGCTGAATCTTTTGAACCTGACATTAACCCT
        G                                                                                    G

5501
ACCCAACACCCTGTTACAAATATATCAGATACATATTTAACTTCCACACCTAATACAGTTACACAACCGTGGGTAACACCACAGTTCCATTGTCAATTC
                                                                                              C

5601                                                                     [L1→
CTAATGACCTGTTTTTACAGTCTGGCCCTGATATAACTTTTCCTACTGCACCTATGGGAACACCCTTTAGTCCTGTAACTCCTGCTTTACCTACAGGCCC
             A

5701
TGTTTTCATTACAGGTTCTGGATTTTATTTGCATCCTGCATGCTATTTTGCACGTAAACGCCGTAAACGTATTCCCTTATTTTTTTCAG<u>AT</u>GTGGCGGCC

←L2]
TAGCGACAGCACAGTATATGTGCCTCCTCCTAACCCTGTATCCAAAGTTGTTGCCACGGATGCTTATGTTACTCGCACCAACATATTTTATCATGCCAGC

5901
AGTTCTAGACTTCTTGCAGTGGGTCATCCTTATTTTTCCATAAAACGGGCTAACAAAACTGTTGTGCCAAAGGTGTCAGGATATCAATACAGAGTATTTA
            A                                                                              G

6001
AGGTGGTCTTACCAGATCCTAACAAATTTGCATTGCCTGACTCGTCTCTTTTTGATCCCACAACACAACGTTTGGTATGGGCATGCACAGGCCTAGAGGT
                                                    C                A

6101
GGGCCCGGGGACAGCCATTAGGTGTGGGTGTAAGTGGACATCCTTTCCTAAATAAATATGATGATGTTGAAAATTCAGGGAGTGGTGGTAACCCTGGACAG
   A

6201
GATAACAGGCGTTAATGTAGGTATGGATTATAAACAAACACAATTATGCATGGTTGGATGTGCCCCCCCCTTTGGGCGAGCATTGGGGTAAAGGTAAACAGT

6301
GTACTAATACACCTGTACAGGCTGGTGACTGCCCGCCCTTAGAACTTATTACCAGTGTTATACAGGATGGCGATATGGTTGACACAGGCTTTGGTGCTAT

6401
GAATTTTGCTGATTTGCAGACCAATAAATCAGATGTTCCTATTGACATATGTGGCACTACATGTAAATATCCAGATTATTTACAAATGGCTGCAGACCCA

FIG.1E

6501
TATGGTGATAGATTATTTTTTTTTCTACGAAGGAACAAATGTTTGCCAGACATTTTTTTTAACAGGGCTGGCGAGGTGGGGGAACCTGTGCCTGATACTC
                                                                                                A

6601
TTATAATTAAGGGTAGTGGAAATCGCACGTCTGTACGGAGTAGTATATATGTTAACACCCCAAGCGGCTCTTTGGTGTCCTCTGAGGCACAATTGTTTAA
                                                                    G

6701
TAAGCCATATTGGCTACAAAAAGCCCAGGGACATAACAATGGTATTTGTTGGGGTAATCAACTGTTTGTTACTGTGGTAGATACCACACGCAGTACCAAC

6801
ATGACATTATGTGCATCCGTAACTACATCTTCCACATACACCAATTCTGATTATAAAGAGTACATGCGTCATGTGGAAGAGTATGATTTACAATTTATTT

6901
TTCAATTATGTAGCATTACATTGTCTCCTGAAGTAATGCCCTATATTCACACAATGAATCCCTCTGTTTTGGAAGACTGGAACTTTGGGTTATCGCCTCC

7001
CCCAAATGGTACATTAGAAGATACCTATAGGTATGTGCAGTCACAGGCCATTACCTGTCAAAAGCCCACTCCTGAAAAGGAAAAGCCAGATCCCTATAAG

7101
AACCTTAGTTTTTGGGAGGTTAATTTAAAAGAAAAGTTTTCTAGTGAATTGGATCAGTATCCTTTGGGACGCAAGTTTTTGTTACAAAGTGGATATAGGG

7201                                                                               ←L1]
GACGGTCCTCTATTCGTACCGGTGTTAAGCGCCCTGCTGTTTCCAAAGCCTCTGCTGCCCCTAAACGTAAGCGCGCCAAAACTAAAAGGTAATATATGTG
              A

7301
TATATGTACTGTTATATATATGTGTGTATGTACTGTTATGTATATGTGTGTATGTACTGTTATATGTATGTGTGTTGTATATATGTGTGTATATATGTGT
                                                                    _____

7401
ATGTGTGTATATGTATATGTATGTGTTGTGTATATATATGTGTGTGTGTGTTATGTGTGTAATGTAATTTATTTGTGTAATGTGTATGTGTGTTTATGTG
_____                       C               G

7501
CAATAAACAATTAACT-------ACACCCTGTGACTCAGTGGCTGTTGCACGCGTTTTGGTTTGCACGCGCCTTACACACATAAGTAATATACATGCACAA
                C  CTTGTT

7595
TATATATATTTTTGTT-ACAATAATATATTTTTATATTTGCAACCGTTTTCGGTTGCCCTTGGCATACACTTTCCACCAATTTGTTACAACGTGTTGCCT
            T A  C   C                                  A                                    T

7694
GTTAATCCTATATATTTTGTGCCAGGTACACATTGCCCTGCCAAGTTCATTGCCAAGTGCATCATATCCTGCCAACCACACACCTGGCGCCAGGGTGCGG
C                                       GC
7794
TATTGCCTTACTCATATGTTTATTGCCACTGCAATAAACCTGTCTTTGTGTTATACTTTTCTGCACTGTAGCCAACTCTTAAAAGCATTTTTGGCTTGTA
         ─────────────────              A
7894
GCAGAACATTTTTTTGCTCTTACTGTTTGGTATACAATAACATAAAAATGAGTAACCTAAGGTCACACACCTGCAACCGGTTTCGGTTATCCACACCCTA
   C                                                                            G
7994
CATATTTCCTTCTTATA

FIG.1G

DNA ENCODING HUMAN PAPILLOMAVIRUS TYPE 6A

CROSS-RELATED TO OTHER APPLICATIONS

This application is a continuation of application Ser. No. 08/983,527, filed Jul. 31, 1997, now abandoned, which is a continuation of application Ser. No. 08/310,468, filed Sep. 22, 1994, now abandoned.

FIELD OF THE INVENTION

The present invention is directed to DNA molecules encoding purified human papillomavirus type 6a and derivatives thereof.

BRIEF DESCRIPTION OF THE DRAWINGS

FIG. 1. HPV6a nucleotide sequence.

BACKGROUND OF THE INVENTION

Papillomavirus (PV) infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. PV are species specific infective agents; a human papillomavirus do not infect a nonhuman animal.

Papillomaviruses may be classified into distinct groups based on the host that they infect. Human papillomaviruses (HPV) are further classified into more than 70 types based on DNA sequence homology. PV types appear to be type-specific immunogens in that a neutralizing immunity to infection by one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause benign condylomata of the genital or respiratory mucosa. HPV types 16 and 18 cause epithelial dysplasia of the genital mucosa and are associated with the majority of in situ and invasive carcinomas of the cervix, vagina, vulva and anal canal.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunological data suggest that most of the L2 protein is internal to the L1 protein. The L1 ORF is highly conserved among different papillomaviruses. The L2 proteins are less conserved among different papillomaviruses.

The L1 and L2 genes have been identified as good targets for immunoprophylactics. Some of the early genes have also been demonstrated to be potential targets of vaccine development. Studies in the cottontail rabbit papillomavirus (CRPV) and bovine papillomavirus (BPV) systems have shown that immunizations with these proteins expressed in bacteria or by using vaccinia vectors protected animals from viral infection. Expression of papillomavirus L1 genes in baculovirus expression systems or using vaccinia vectors resulted in the assembly of virus-like particles (VLP) which have been used to induce high-titer virus-neutralizing antibody responses that correlate with protection from viral challenge.

HPV6 and HPV 11, which are only rarely associated with malignancies, are the causative agents of ~90% of condyloma acuminata, benign lesions of the respiratory and genital mucosa. HPV6 is detected three times more often in these lesions than HPV 11.

The complete nucleotide sequence of HPV6b, the original HPV6 isolate, has been determined (Schwarz, E., et al. 1983. EMBO J. 2:2341–8.). Other HPV6 subtypes have been identified on the basis of restriction enzyme digest patterns (Gissmann, L., et al. 1983. Proc. Natl. Acad. Sci. USA 80:560–3; Mounts, P., et al. 1982. Proc. Natl. Acad. Sci. USA 79:5425–9).

Several groups have demonstrated that HPV6a is the predominant subtype found in condyloma acuminatum biopsies from patients in the U.S. and Europe. A recent report suggests that HPV6a is the HPV6 prototype (Kitasato, H., et al. 1994. J. Gen. Virol. 75:1157–1162). It is estimated that in the U.S. alone approximately one percent of all men and women in the 15 to 49 year age group present to physicians with condyloma acuminatum. Unfortunately, there is no effective treatment for HPV-related disease. Therefore, a vaccine would be highly desirable. For the development of a prophylactic or therapeutic vaccine however, the sequence determination of late and early genes of the most common HPV subtypes is of critical importance.

The limited sequence information about HPV6a concerns the long control region (LCR) and the E6 and E7 ORFs. The instant application describes the cloning of HPV6a from a condyloma acuminatum biopsy, the determination of its complete viral DNA sequence and the corresponding amino acid sequences of the major HPV6a open reading frames (ORFs).

The present invention is directed to DNA molecules encoding purified human papillomavirus type 6a (HPV type 6a; HPV6a) and uses of the DNA molecules.

SUMMARY OF THE INVENTION

The present invention is directed to DNA molecules encoding purified human papillomavirus type 6a (HPV type 6a; HPV6a) and derivatives thereof.

DETAILED DESCRIPTION OF THE INVENTION

The present invention is directed to DNA molecules encoding purified human papillomavirus type 6a (HPV type 6a; HPV6a) and derivatives thereof. Such derivatives include but are not limited to peptides and proteins encoded by the DNA, antibodies to the DNA or antibodies to the proteins encoded by the DNA, vaccines comprising the DNA or vaccines comprising proteins encoded by the DNA, immunological compositions comprising the DNA or the proteins encoded by the DNA, kits containing the DNA or RNA derived from the DNA or proteins encoded by the DNA.

HPV6 is the principal causative agent of condyloma acuminata (benign lesions of the respiratory and genital mucosa). The complete nucleotide sequence of HPV6b, the original HPV6 isolate, has been determined Other HPV6 subtypes have been identified on the basis of restriction enzyme digest patterns.

Several groups have demonstrated that HPV6a is the predominant subtype found in condyloma acuminatum biopsies from patients in the U.S. and Europe. It is estimated that in the U. S. alone approximately one percent of all men and women in the 15 to 49 year age group present to physicians with condyloma acuminatum. Unfortunately, there is no effective treatment for HPV-related disease. Therefore, a vaccine would be highly desirable. For the development of a prophylactic or therapeutic vaccine however, the sequence determination of late and early genes of the most common HPV subtypes is of critical importance.

The limited sequence information about HPV6a concerns the long control region (LCR) and the E6 and E7 ORFs. The instant application describes the cloning of HPV6a from a condyloma acuminatum biopsy, the determination of its complete viral DNA sequence and the corresponding amino acid sequences of the major HPV6a open reading frames (ORFs). The present invention is directed to DNA molecules encoding purified human papillomavirus type 6 and derivatives of the DNA molecules.

Pharmaceutically useful compositions comprising the DNA or proteins encoded by the DNA may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein or VLP. Such compositions may contain proteins or VLP derived from more than one type of HPV.

Therapeutic or diagnostic compositions of the invention are administered to an individual in amounts sufficient to treat or diagnose PV infections. The effective amount may vary according to a variety of factors such as the individual's condition, weight, sex and age. Other factors include the mode of administration. Generally, the compositions will be administered in dosages ranging from about 1 $\mu$g to about 1 $\mu$g.

The pharmaceutical compositions may be provided to the individual by a variety of routes such as subcutaneous, topical, oral, mucosal, intravenous and intramuscular.

The vaccines of the invention comprise DNA, RNA or proteins encoded by the DNA that contain the antigenic determinants necessary to induce the formation of neutralizing antibodies in the host. Such vaccines are also safe enough to be administered without danger of clinical infection; do not have toxic side effects; can be administered by an effective route; are stable; and are compatible with vaccine carriers.

The vaccines may be administered by a variety of routes, such as orally, parenterally, subcutaneously, mucosally, intravenously or intramuscularly. The dosage administered may vary with the condition, sex, weight, and age of the individual; the route of administration; and the type PV of the vaccine. The vaccine may be used in dosage forms such as capsules, suspensions, elixirs, or liquid solutions. The vaccine may be formulated with an immunologically acceptable carrier.

The vaccines are administered in therapeutically effective amounts, that is, in amounts sufficient to generate a immunologically protective response. The therapeutically effective amount may vary according to the type of PV. The vaccine may be administered in single or multiple doses.

The DNA and DNA derivatives of the present invention may be used in the formulation of immunogenic compositions. Such compositions, when introduced into a suitable host, are capable of inducing an immune response in the host.

The DNA or its derivatives may be used to generate antibodies. The term "antibody" as used herein includes both polyclonal and monoclonal antibodies, as well as fragments thereof, such as, Fv, Fab and F(ab)2 fragments that are capable of binding antigen or hapten.

The DNA and DNA derivatives of the present invention may be used to serotype HPV infection and HPV screening. The DNA, recombinant proteins, VLP and antibodies lend themselves to the formulation of kits suitable for the detection and serotyping of HPV. Such a kit would comprise a compartmentalized carrier suitable to hold in close confinement at least one container. The carrier would further comprise reagents such as HPV6a DNA, recombinant HPV protein or VLP or anti-HPV antibodies suitable for detecting a variety of HPV types. The carrier may also contain means for detection such as labeled antigen or enzyme substrates or the like.

The DNA and derived proteins therefrom are also useful as molecular weight and molecular size markers.

Because the genetic code is degenerate, more than one codon may be used to encode a particular amino acid, and therefore, the amino acid sequence can be encoded by any of a set of similar DNA oligonucleotides. Only one member of the set will be identical to the HPV6a sequence but will be capable of hybridizing to HPV6a DNA even in the presence of DNA oligonucleotides with mismatches under appropriate conditions. Under alternate conditions, the mismatched DNA oligonucleotides may still hybridize to the HPV6a DNA to permit identification and isolation of HPV6a encoding DNA.

The purified HPV6a DNA of the invention or fragments thereof may be used to isolate and purify homologues and fragments of HPV6a from other sources. To accomplish this, the first HPV6a DNA may be mixed with a sample containing DNA encoding homologues of HPV6a under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site-directed mutagenesis.

As used herein, a "functional derivative" of HPV6a is a compound that possesses a biological activity (either functional or structural) that is substantially similar to the biological activity of HPV6a. The term "functional derivatives" is intended to include the "fragments," "variants," "degenerate variants," "analogs" and "homologues" or to "chemical derivatives" of HPV6a. The term "fragment" is meant to refer to any polypeptide subset of HPV6a. The term "variant" is meant to refer to a molecule substantially similar in structure and function to either the entire HPV6a molecule or to a fragment thereof. A molecule is "substantially similar" to HPV6a if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "functional derivative" does not include HPV6b.

The term "analog" refers to a molecule substantially similar in function to either the entire HPV6a molecule or to a fragment thereof.

A variety of procedures may be used to molecularly clone HPV6a DNA. These methods include, but are not limited to, direct functional expression of the HPV6a genes following the construction of a HPV6a-containing cDNA or genomic DNA library in an appropriate expression vector system. Another method is to screen HPV6a-containing cDNA or genomic DNA library constructed in a bacteriophage or plasmid shuttle vector with a labeled oligonucleotide probe designed from the amino acid sequence of the HPV6a. An additional method consists of screening a HPV6a-containing cDNA or genomic DNA library constructed in a bacteriophage or plasmid shuttle vector with a partial DNA encoding the HPV6a. This partial DNA is obtained by the specific polymerase chain reaction (PCR) amplification of HPV6a DNA fragments through the design of degenerate oligonucleotide primers from the amino acid sequence of purified HPV6a. Another method is to isolate RNA from HPV6a-producing cells and translate the RNA into protein via an in vitro or an in vivo translation system. The translation of the RNA into a peptide or a protein will result in the production of at least a portion of HPV6a protein which can be identified by, for example, the activity of HPV6a protein or by immunological reactivity with an anti-HPV6a antibody. In this method, pools of RNA isolated from HPV6a-producing cells can be analyzed for the presence of an RNA which encodes at least a portion of the HPV6a. Further fractionation of the RNA pool can be done to purify the HPV6a RNA from non-HPV6a RNA. The peptide or protein produced by this method may be analyzed to provide amino acid sequences which in turn are used to provide primers for production of HPV6a cDNA, or the RNA used for translation can be analyzed to provide nucleotide sequences encoding HPV6a and produce probes for the screening of a HPV6a cDNA library. These methods are known in the art and can be found in, for example, Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.

It is apparent that other types of libraries, as well as libraries constructed from other cells or cell types, may be useful for isolating HPV6a-encoding DNA. Other types of libraries include, but are not limited to, cDNA libraries derived from other cells or cell lines containing HPV type 6a and genomic DNA libraries.

Preparation of cDNA libraries can be performed by a variety of techniques. cDNA library construction techniques can be found for example, Sambrook, J., et al., supra. It is apparent that DNA encoding HPV6a may also be isolated from a suitable genomic DNA library. Construction of genomic DNA libraries can be performed by a variety of techniques. Genomic DNA library construction techniques can be found in Sambrook, J., et al. supra.

The cloned HPV6a DNA or fragments thereof obtained through the methods described herein may be recombinantly expressed by molecular cloning into an expression vector containing a suitable promoter and other appropriate transcription regulatory elements, and transferred into prokaryotic or eukaryotic host cells to produce recombinant HPV6a. Techniques for such manipulations are fully described in Sambrook, J., et al., supra, and are known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells. Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express HPV6a DNA or fragments thereof in mammalian cells. Commercially available mammalian expression vectors which may be suitable for recombinant HPV6a expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8–2) (ATCC 37110), pdBPV-MMTneo(342–12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express HPV6a DNA or fragments thereof in bacterial cells. Commercially available bacterial expression vectors which may be suitable include, but are not limited to pET11a (Novagen), lambda gt11 (Invitrogen), pcDNAII (Invitrogen), pKK223-3 (Pharmacia).

A variety of fungal cell expression vectors may be used to express HPV6a or fragments thereof in fungal cells. Commercially available fungal cell expression vectors which may be suitable include but are not limited to pYES2 (Invitrogen) and Pichia expression vector (Invitrogen).

A variety of insect cell expression vectors may be used to express HPV6a DNA or fragments thereof in insect cells. Commercially available insect cell expression vectors which may be suitable include but are not limited to pBlue Bac m (Invitrogen).

An expression vector containing DNA encoding HPV6a or fragments thereof may be used for expression of HPV6a proteins or fragments of HPV6a proteins in a cell, tissues, organs, or animals (including humans). Host cells may be prokaryotic or eukaryotic, including but not limited to bacteria such as E.coli, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK⁻) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce HPV6a protein. Identification of HPV6a expressing host cell clones may be done by several means, including but not limited to immunological reactivity with anti-HPV6a antibodies, and the presence of host cell-associated HPV6a activity, such as HPV6a-specific ligand binding or signal transduction defined as a response mediated by the interaction of HPV6a-specific ligands at the HPV6a.

Expression of HPV DNA fragments may also be performed using in vitro produced synthetic mRNA or native mRNA. Synthetic mRNA or mRNA isolated from HPV6a producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of HPV6a protein(s) in a host cell, HPV6a protein may be recovered to provide HPV6a in purified form. Several HPV6a purification procedures are available and suitable for use. As described herein, recombinant HPV6a protein may be purified from cell lysates and extracts by various combinations of, or individual application of salt fractionation, ion exchange chromatography, size exclusion chromatography, hydroxylapatite adsorption chromatography and hydrophobic interaction chromatography.

In addition, recombinant HPV6a may be separated from other cellular proteins by use of an immunoaffinity column made with monoclonal or polyclonal antibodies specific for full length nascent HPV6a, or polypeptide fragments of HPV6a. Monoclonal and polyclonal antibodies may be prepared according to a variety of methods known in the art. Monoclonal or monospecific antibody as used herein is defined as a single antibody species or multiple antibody species with homogenous binding characteristics for HPV6a. Homogenous binding as used herein refers to the ability of the antibody species to bind to a specific antigen or epitope.

It is apparent that the methods for producing monospecific antibodies may be utilized to produce antibodies specific for HPV6a polypeptide fragments, or full-length nascent HPV6a polypeptide. Specifically, it is apparent that monospecific antibodies may be generated which are specific for the fully functional HPV6a or fragments thereof.

The present invention is also directed to methods for screening for compounds which modulate the expression of DNA or RNA encoding HPV6a as well as the function(s) of HPV6a protein(s) in vivo. Compounds which modulate these activities may be DNA, RNA, peptides, proteins, or non-proteinaceous organic molecules. Compounds may modulate by increasing or attenuating the expression of DNA or RNA encoding HPV6a, or the function of HPV6a protein. Compounds that modulate the expression of DNA or RNA encoding HPV6a or the function of HPV6a protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing HPV6a DNA, fragments of HPV6a DNA, antibodies to HPV6a DNA or HPV6a protein, HPV6a RNA or HPV6a protein may be prepared. Such kits are used to detect DNA which hybridizes to HPV6a DNA or to detect the presence of HPV6a protein(s) or peptide fragments in a sample. Such characterization is useful for a variety of purposes including but not limited to forensic analyses and epidemiological studies.

Nucleotide sequences that are complementary to the HPV6a encoding DNA sequence may be synthesized for antisense therapy. These antisense molecules may be DNA, stable derivatives of DNA such as phosphorothioates or methylphosphonates, RNA, stable derivatives of RNA such as 2'-O-alkylRNA, or other HPV6a antisense oligonucleotide mimetics. HPV6a antisense molecules may be introduced into cells by microinjection, liposome encapsulation or by expression from vectors harboring the antisense sequence. HPV6a antisense therapy may be particularly useful for the treatment of diseases where it is beneficial to reduce HPV6a activity.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the HPV6a or its activity while minimizing any potential toxicity. In addition, co-administration or sequential administration of other agents may be desirable.

Advantageously, compounds of the present invention may be administered in a single daily dose, or the total daily dosage may be administered in several divided doses. Furthermore, compounds for the present invention may be administered via a variety of routes including but not limited to intranasally, transdermally, by suppository, orally, and the like.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following examples illustrate the present invention without, however, limiting the same thereto.

EXAMPLE 1

Extraction of Nucleic Acid from Biopsy.

A large vulvar condyloma acwninatum lesion was obtained from a 25 year old, post partum female patient. A fragment of the lesion was frozen in liquid nitrogen, then processed with a Braun mikro-dismembrator II (B. Braun Instruments, Melsungen, Germany). The resulting material was solubilized with 0.6% (w/v) sodium dodecyl sulfate (SDS), treated with proteinase K (50 µg/ml), and extracted with phenol/chloroform/isoamyl alcohol. DNA was ethanol-precipitated and quantified by UV spectrophotometry. The presence of high-molecular-weight DNA was established by agarose gel electrophoresis followed by staining with ethidium bromide.

EXAMPLE 2

Typing of HPV DNA.

The HPV DNA type was determined using the hybrid capture assay marketed as ViraType Plus (Digene Diagnostics, Beltsville, Md.). The HPV probes used were divided into two pools whose composition is based on the association of each type with genital tract malignancies. Probe group A contained the "low-risk" types HPV6, 11, 42,43, and 44 while probe B contained the "high-risk" types 16, 18, 31, 33, 35, 45, 51, 52, and 56. Total DNA was digested with PstI, BamHI, and HindIII and Southern blots were performed under high stringency conditions ($T_m$–50° C.) to determine the HPV subtype.

EXAMPLE 3

Cloning of HPV6a Genome.

Total DNA extracted from the HPV6a-positive biopsy sample was digested with HindIII endonuclease. Following size-fractionation through a 0.8% low-melting-temperature agarose preparative gel, a region corresponding to DNA of ~8 kilobase pairs (kbp) was excised from the gel and the agarose was digested with Gelase$^{TM}$ enzyme (Epicentre Technologies, Inc., Madison, Wis.). The sample was ligated with pUC18 (Pharmacia, Inc., Piscataway, N.J.) which had been digested with HindUl and dephosphorylated . Following transformation of competent *E. coli* DH5 cells (Gibco, BRL, Gaithersburg, Md.), the plasmid library was screened for HPV6a-positive clones by colony-hybridization using an antisense $^{32}$P-labeled oligonucleotide that was complementary to the 3'-end of the HPV6b L1 gene (5'-GAG AGA TCT TAC CTT TTA GTT TTG GCG CGC TTA C-3'; SEQ ID NO:1). A pUC18 plasmid containing the 8.1-kbp HPV6a genome was isolated and characterized by restriction enzyme and Southern blot analyses. This plasmid was designated pUCI 8-HPV6a. Plasmid DNA was prepared using the Qiagen$^{TM}$ Plasmid Maxi kit (Qiagen Inc., Chatsworth, Calif.).

EXAMPLE 4

Sequence Analysis of pUC1 8-HPV6a.

To determine the complete HPV6a sequence, sequencing primers were synthesized based on the published HPV6b sequence. Both strands of the complete 8.1-kbp HPV6a genome were sequenced by the dideoxy chain termination method using the PRISM™ kit and an Applied Biosystems (ABI) automated sequencer (#373A) according to the manufacturers' instructions (ABI, Inc., Foster City, Calif.). In cases where the sense and antisense sequence did not match, additional HPV6a specific primers were synthesized to resequence in both directions over the area in question to obtain a consensus.

The complete HPV6a sequence in comparison to the published HPV6b sequence is shown in FIG. 1. Bases shown below the HPV6a sequence correspond to the HPV6b sequence. The DNA sequences of HPV6a and HPV6b exhibited over 97% identity with a total of 229 bp changes identified out of 8010 bp. The most significant differences compared to the HPV6b sequence were found in the LCR (nt 7205–nt 106). Apart from several single nucleotide (nt) changes in the HPV6a LCR, a 94-bp insertion at nt 7350 and another 19-bp insertion at nt 7804 were found. At nt 7615, six base pairs were deleted from the HPV6a genome.

EXAMPLE 5

HPV6a Sequence Variation of ORFs Compared to HPV6b.

Open reading frames were determined in the HPV6a sequence and the major ORFs translated into amino acid sequences and compared to the respective HPV6b sequences.

The major capsid protein Li was the only ORF identical to the HPV6b sequence. All other ORFs showed amino acid changes which are summarized in Table 1. The minor capsid protein L2 showed five amino acid changes; the E6 and E7 ORFs showed one amino acid change each. In the E1 protein six amino acids and in the E2 protein 11 amino acids were different. In the E4 protein four amino acid changes were detected. The E5a ORF had changes in four positions, the ORF E5b in seven positions.

TABLE 1

Sequence variation in the HPV6a ORFs E6, E7, E1, E2, E4, E5, and L2 compared to HPV6b

| Open reading frame | Position (nucleotide) | Position (amino acid) | Amino acid change |
|---|---|---|---|
| E6 | 252 | 50 | His→Gln |
| E7 | 792 | 88 | Asp→Asn |
| E1 | 1535, 1536 | 235 | Leu→Ala |
|  | 1670 | 280 | Leu→Val |
|  | 1741 | 303 | Glu→Asp |
|  | 2208 | 459 | Thr→Ser |
|  | 2557 | 575 | Asp→Glu |
|  | 2654 | 608 | Thr→Ala |
| E2 | 2802 | 27 | His→Asp |
|  | 2974 | 94 | Arg→Lys |
|  | 3148 | 142 | Asn→Thr |
|  | 3153 | 144 | Thr→Ser |
|  | 3272 | 193 | His→Gln |
|  | 3388 | 222 | Leu→Pro |
|  | 3405 | 227 | Lys→Gln |
|  | 3643 | 307 | Arg→Lys |
|  | 3693 | 324 | Ser→Pro |
|  | 3735 | 338 | Asp→His |
|  | 3765 | 348 | Asp→Asn |
|  | 3794 | 357 | Ser→Arg |
| E4 | 3272 | 6 | Ile→Asn |
|  | 3388 | 60 | Gly→Glu |
|  | 3461 | 69 | Pro→His |
|  | 3552 | 99 | Asp→Glu |
| E5a | 3935 | 16 | Phe→Leu |
|  | 4004 | 40 | Glu→Asp |
|  | 4137 | 84 | Tyr→His |
|  | 4150 | 88 | Thr→Asn |
| E5b | 4235 | 25 | Met→Val |
|  | 4297 | 45 | Lys→Asn |
|  | 4314 | 51 | Asn→Thr |
|  | 4323 | 54 | Asp→Ala |
|  | 4343 | 61 | Tyr→His |
|  | 4346,4347 | 62 | Thr→Asp |
|  | 4353 | 64 | Asp→Ala |
| L2 | 4646,4647 | 75 | Gln→Gly |
|  | 4976 | 185 | Val→Ile |
|  | 5021 | 200 | Val→Ile |
|  | 5490 | 356 | Gly→Asp |
|  | 5597 | 392 | Leu→Ile |

EXAMPLE 6

Sub-cloning of the HPV6a cDNA into Expression Vectors

The cDNA enncoding HPV6a is sub-cloned into several vectors for exprexion of the HPV6a protein in transfected host cells and for in vitro transcription/translation. These vectors include pBluescript II SK+(where expresion is driven by T7 or T3 promoters) pcDNA I/Amp (where expression is driven by the cytomegalovirus (CMV) promoter), pSZ9016-1 (where expression is driven by the HIV long terminal repeat (LTR) promoter) and the baculovirus transfer vector pVL1393 (where expresion is driven by the polyhedrin (PH) promoter) for producing recombinant baculovirus containing the HPV6a encoding DNA sequence.

a) pBluescript II SK+:HPV6a. The full length HPV6a cDNA clone is retrived from lambda bacteriophage by limited Eco RI digestion and ligated into Eco RI-cut, CIP-treated pBluescript II SK+. Separate subclones are recovered in which the sense orientation of HPV6a followed either the T7 or T3 promoters.

b)pcDNA I/Amp:HPV6a. To facilitate directional cloning, HPV6a is excised from a purified plasmid preparation of pBluescript II SK+:HPV6a in which the HPV6a DNA sequence is downstream of the T7 promoter using Eco RV and Xba I. The resulting Eco RV, Xba I HPV6a fragment is purified and ligated into Eco RV-cut, Xba I-cut, CIP-treated pcDNA I/Amp such that the HPV6a encoding DNA is downstream of the CMV promoter.

c)pSZ9016-1:HPV6a. HPV6a is excised from pBluescript II SK+:HPV6a by limited Eco RI digestion and subsequent purification of the 1.3 Kb fragment from agarose gels. The resulting Eco RI HPV6a fragment is ligated into Eco RI-cut, CIP-treated pSZ9016-1. Subclones are selected in which the sense orientation of HPV6a is downstream of the HIV LTR promoter.

d)pVL1393:HPV6a and pVL1393:T7 HPV6a HA

Directional cloning of the HPV6a encoding DNA into the baculovirus transfer vector pVL1393 is mediated by excising HPV6a from pcDNA I/Amp:HPV6a with Bam HI and Xba I then ligating the resulting 1.3 Kb fragment into Bam HI-cut, Xba I-cut, CIP-treated pVL1393 producing pVL1393:HPV6a. Similarly, HPV6a is epitope tagged by engineering a T7 tag at the 5' amino terminus of the HPV6a open reading frame and a FluHA epitope at the 3' carboxy terminus. The HPV6a DNA modified in this manner is ligated into the Bam HI/Xba I sites of pVL1393 to produce pVL1393:T7HPV6a HA.

EXAMPLE 7

Expression Of The HPV6a Polypeptide By In Vitro Transcription/Translation And BY Transfection Into Host Cells Vectors containing HPV DNA sequences are used to drive the translation of the HPV6a polypeptide in rabbit reticulocyte lysates, mammalian host cells, and in baculovirus infected insect cells. The experimental procedures are essentially those outlined in the manufacturers' instructions.

a) In vitro Transcription/Translation. pBluescript III SK+:HPV6a plasmid DNA (with HPV6a in the T7 orientation) is linearized by Bam HI digestion downstream of the HPV6a insert. The linearized plasmid is purified and used as a template for run-off transcription using T7 RNA polymerase in the presence of m7G(5') ppp(5')G. The resulting capped HPV6a transcripts are purified by LiCl precipitation and used to drive the translation of HPV6a in nuclease-pretreated rabbit reticulocyte lysate in the presence of L-[$^{35}$S] methionine.

b) Expression in Mammalian Cells. The HPV6a protein is expressed in mammalian host cells following transfection with either pcDNA I/VAmp:HPV6a (under control of the CMV promoter) or pSZ9016-1:HPV6a (under control of the HIV LTR promoter). In the latter case (pSZ9016-1 :HPV6a), cells are co-transfected with the TAT expressing plasmid pSZ9016-1 :TAT. For both HPV6a expression plasmids, COS-7 cells are transfected using either DEAE-dextran or lipofection with Lipofectamine (BRL).

c) Expression in Insect Cells. The HPV6a - containing baculovirus transfer vector pVL1393:T7 HPV6a HA is used to produce recombinant baculovirus (*Autographa californica*) by in vivo homologous recombination. Epitope tagged HPV6a is then expressed in Sf9 (*Spodoptera frugiperda*) insect cells grown in suspension culture following infection with the HPV6a - containing recombinant baculovirus.

EXAMPLE 8

Compounds that affect HPV6a activity may be detected by a variety of methods. A method of identifying compounds that affect HPV6a comprises:

(a) mixing a test compound with a solution containing HPV6a to form a mixture;

(b) measuring HPV6a activity in the mixture; and (c) comparing the HPV6a in the mixture to a standard.

Compounds that affect HPV6a activity may be formulated into pharmaceutical compositions. Such pharmaceutical compositions may be useful for treating diseases or conditions that are characterized by HPV6a infection.

EXAMPLE 9

DNA which is structurally related to DNA encoding HPV6a is detected with a probe. A suitable probe may be derived from DNA having all or a portion of the nucleotide sequence of FIG. 1, RNA encoded by DNA having all or a portion of the nucleotide sequence of FIG. 1 or degenerate oligonucleotides derived from a portion of the sequence of FIG. 1.

What is claimed is:

1. An isolated DNA encoding a single HPV6a protein, wherein the HPV6a protein is selected form the group consisting of: HPV6a L2 (encoded by nucleotides 4380–5804 of SEQ ID NO:2), HPV6a E1 (encoded by nucleotides 717–2781 of SEQ ID NO:2), HPV6a E2 (encoded by nucleotides 2697–3829 of SEQ ID NO:2), HPV6a E4 (encoded by nucleotides 3242–3584 of SEQ ID NO:2), HPV6a E5 (encoded by nucleotides 3242–3584 of SEQ ID NO:2), HPV6a E6 (encoded by nucleotides 32–554 of SEQ ID NO:2), and HPV6a E7 (encoded by nucleotides 442–826 of SEQ ID NO:2), wherein the DNA is under transcriptional control of a heterologous promoter.

2. A vector comprising DNA encoding a single human Papillomavirus 6a (HPV6a) protein, wherein the DNA consists of a sequence selected from the group consisting of: HPV6a L2 (nucleotides 4380–5804 of SEQ ID NO:2), HPV6a E1 (nucleotides 717–2781 of SEQ ID NO:2), HPV6a E2 (nucleotides 2697–3829 of SEQ ID NO:2), HPV6a E4 (nucleotides 3242–3584 of SEQ ID NO:2), HPV6a E5 (nucleotides 3888–4163 of SEQ ID NO:2), HPV6a E6 (nucleotides 32–554 of SEQ ID NO:2), and HPV6a E7 (nucleotides 442–826 of SEQ ID NO:2).

3. A host cell comprising a vector according to claim 2.

4. A host cell according to claim 3 which is selected from the group consisting of: yeast, insect, and mammalian cells.

5. A host cell according to claim 4 which is a yeast cell.

6. An immunogenic composition comprising DNA encoding a single HPV6a protein, wherein the BPV6a protein is selected from the group consisting of: HPV6a L2 (encoded by nucleotides 4380–804 of SEQ ID NO:2), HPV6a E1 (encoded by nucleotides 717–2781 of SEQ ID NO:2), HPV6a E2 (encoded by nucleotides 2697–3829 of SEQ ID NO:2), HPV6a E4 (encoded by nucleotides 3242–3584 of SEQ ID NO:2), HPV6a E5 (encoded by nucleotides 3242–3584 of SEQ ID NO:2), HPV6a E6 (encoded by nucleotides 32–554 of SEQ ID NO:2), and HPV6a E7 (encoded by nucleotides 442–826 of SEQ ID NO:2).

7. An immunogenic composition according to claim 6, wherein the DNA encoding the HPV6a protein are present in a vector.

8. An immunogenic composition according to claim 7 wherein the composition is formulated with an immunologically acceptable carrier.

9. A method of making a protein composition comprising:

a) transferring a vector comprising a DNA encoding a single HPV 6a protein selected form the group consisting of: HPV6a L2 (nucleotides 4380–5804 of SEQ ID NO:2), HPV6a E1 (nucleotides 717–2781 of SEQ ID NO:2), HPV6a E2 (nucleotides 2697–3829 of SEQ ID NO:2), HPV6a E4 (nucleotides 3242–3584 of SEQ ID NO:2), HPV6a E5 (nucleotides 3242–3584 of SEQ ID NO:2), HPV6a E6 (nucleotides 32–554 of SEQ ID NO:2), and HPV6a E7 (nucleotides 442–826 of SEQ ID NO:2) to a host cell, and b) culturing the host cell under conditions which allow expression of the HPV6a protein from the vector.

10. A method according to claim 9 wherein the host cell is selected from the group consisting of: yeast, insect, and mammalian cells.

11. A method according to claim 10, further comprising the step of purifying the protein so produced.

12. A method according to claim 10, further comprising the step of formulating the protein with an immunologically acceptable carrier.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

GAGAGATCTT ACCTTTTAGT TTTGGCGCGC TTAC      34

(2) INFORMATION FOR SEQ ID NO:2:

(i) SEQUENCE CHARACTERISTICS:
      (A) LENGTH: 8010 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
GTTAATAACA ATCTTGGTTT TAAAAAATAG GAGGGACCGA AAACGGTTCA ACCGAAAACG    60

GTTGTATATA AACCAGCCCT AAAATTTAGC AAACGAGGCA TTATGGAAAG TGCAAATGCC   120

TCCACGTCTG CAACGACCAT AGACCAGTTG TGCAAGACGT TTAATCTATC TATGCATACG   180

TTGCAAATTA ATTGTGTGTT TTGCAAGAAT GCACTGACCA CTGCAGAGAT TTATTCATAT   240

GCATATAAAC AGCTAAAGGT CCTGTTTCGA GGCGGCTATC CATATGCAGC CTGCGCGTGC   300

TGCCTAGAAT TTCATGGAAA AATCAACCAA TATAGACACT TTGATTATGC TGGATATGCA   360

ACAACTGTTG AAGAAGAAAC TAAACAAGAC ATTTTAGACG TGCTAATTCG GTGCTACCTG   420

TGTCACAAAC CGCTGTGTGA AGTAGAAAAG GTAAAACATA TACTAACCAA GGCGCGGTTT   480

ATAAAGCTAA ATTGTACGTG GAAGGGTCGC TGCCTACACT GCTGGACAAC ATGCATGGAA   540

GACATGTTAC CCTAAAGGAT ATTGTATTAG ACCTGCAACC TCCAGACCCT GTAGGGTTAC   600

ATTGCTATGA GCAATTAGTA GACAGCTCAG AAGATGAGGT GGACGAAGTG GACGGACAAG   660

ATTCACAACC TTTAAAACAA CATTTCCAAA TAGTGACCTG TTGCTGTGGA TGTGACAGCA   720

ACGTTCGACT GGTTGTGCAG TGTACAGAAA CAGACATCAG AGAAGTGCAA CAGCTTCTGT   780

TGGGAACACT AGACATAGTG TGTCCCATCT GCGCACCGAA GACATAACAA CGATGGCGGA   840

CGATTCAGGT ACAGAAAATG AGGGGTCTGG GTGTACAGGA TGGTTTATGG TAGAAGCTAT   900

AGTGCAACAC CCAACAGGTA CACAAATATC AGACGATGAG GATGAGGAGG TGGAGGACAG   960

TGGGTATGAC ATGGTGGACT TTATTGATGA CAGCAATATT ACACACAATT CCTTGGAAGC  1020

ACAGGCATTG TTTAACAGGC AGGAGGCGGA CACCCATTAT GCGACTGTGC AGGACCTAAA  1080

ACGAAAGTAT TTAGGTAGTC CATATGTTAG TCCTATAAAC ACTATAGCCG AGGCAGTGGA  1140

AAGTGAAATA GTCCACGAT TGGACGCCAT TAAACTTACA AGACAGCCAA AAAAGGTAAA  1200

GCGACGGCTG TTTCAAACCA GGGAACTAAC GGACAGTGGA TATGGCTATT CTGAAGTGGA  1260

AGCTGGAACG GGAACGCAGG TAGAGAAACA TGGCGTCCCG GAAAATGGGG GAGATGGTCA  1320

GGAAAAGGAC ACAGGAAGGG ACATAGAGGG GGAGGAACAT ACAGAGGCGG AAGCGCCCAC  1380

AAACAGTGTA CGGGAGCATG CAGGCACAGC AGGAATATTG GAATTGCTAA AATGTAAAGA  1440

TTTACGGGCA GCATTACTTG GTAAGTTTAA AGAATGCTTT GGGCTGTCTT TTATTGATTT  1500

AATTAGGCCA TTTAAAAGTG ATAAAACAAC ATGTGCAGAC TGGGTGGTAG CAGGATTTGG  1560

TATACATCAT AGCATATCAG AGGCATTTCA AAAATTAATT GAGCCATTAA GTTTATATGC  1620

ACATATACAA TGGCTAACAA ATGCATGGGG AATGGTATTG TTAGTATTAG TAAGATTTAA  1680

AGTAAATAAA AGTAGAAGTA CCGTTGCACG TACACTTGCA ACGCTATTAA ATATACCTGA  1740

CAATCAAATG TTAATAGAGC CACCAAAAAT ACAAAGTGGT GTTGCAGCCC TGTATTGGTT  1800

TCGTACAGGT ATATCAAATG CCAGTACAGT TATAGGGGAA GCACCAGAAT GGATAACACG  1860

CCAAACTGTT ATTGAACATG GGTTGGCAGA CAGTCAGTTT AAATTAACAG AAATGGTGCA  1920

GTGGGCATAT GATAATGACA TATGCGAGGA GAGTGAAATT GCATTTGAAT ATGCACAAAG  1980

GGGAGATTTT GATTCTAATG CACGAGCATT TTTAAATAGC AATATGCAGG CAAAATATGT  2040

GAAAGATTGT GCAACTATGT GTAGACATTA TAAACATGCA GAAATGAGGA AGATGTCTAT  2100

AAAACAATGG ATAAAACATA GGGGTTCTAA AATAGAAGGC ACAGGAAATT GGAAACCAAT  2160

TGTACAATTC CTACGACATC AAAATATAGA ATTTATTCCA TTTTTAAGTA AATTTAAATT  2220

ATGGCTGCAC GGTACGCCAA AAAAAAACTG CATAGCCATA GTAGGCCCTC CAGATACTGG  2280

GAAATCGTAC TTTTGTATGA GTTTAATAAG CTTTTTAGGA GGTACAGTTA TTAGTCATGT  2340
```

```
AAATTCCAGC AGCCATTTTT GGTTGCAACC GTTAGTAGAT GCTAAGGTAG CATTGTTAGA    2400

TGATGCAACA CAGCCATGTT GGATATATAT GGATACATAT ATGAGAAATT TGTTAGATGG    2460

TAATCCTATG AGTATTGACA GAAAGCATAA AGCATTGACA TTAATTAAAT GTCCACCTCT    2520

GCTAGTAACG TCCAACATAG ATATTACTAA AGAAGAGAAA TATAAGTATT TACATACTAG    2580

AGTAACAACA TTTACATTTC CAAATCCATT CCCTTTTGAC AGAAATGGGA ATGCAGTGTA    2640

TGAACTGTCA AATGCAAACT GGAAATGTTT TTTTGAAAGA CTGTCGTCAA GCCTAGACAT    2700

TCAGGATTCA GAGGACGAGG AAGATGGAAG CAATAGCCAA GCGTTTAGAT GCGTGCCAGG    2760

AACAGTTGTT AGAACTTTAT GAAGAAAACA GTACTGACCT AAACAAACAT GTATTGCATT    2820

GGAAATGCAT GAGACATGAA AGTGTATTAT TATATAAAGC AAAACAAATG GGCCTAAGCC    2880

ACATAGGAAT GCAAGTAGTG CCACCATTAA AGGTGTCCGA AGCAAAAGGA CATAATGCCA    2940

TTGAAATGCA AATGCATTTA GAATCATTAT TAAAGACTGA GTATAGTATG GAACCGTGGA    3000

CATTACAAGA AACAAGTTAT GAAATGTGGC AAACACCACC TAAACGCTGT TTTAAAAAAC    3060

GGGGCAAAAC TGTAGAAGTT AAATTTGATG GCTGTGCAAA CAATCAATG GATTATGTGG    3120

TATGGACAGA TGTGTATGTG CAGGACACTG ACTCCTGGGT AAAGGTGCAT AGTATGGTAG    3180

ATGCTAAGGG TATATATTAC ACATGTGGAC AATTTAAAAC ATATTATGTA AACTTTGTAA    3240

AAGAGGCAGA AAAGTATGGG AGCACCAAAC AATGGGAAGT ATGTTATGGC AGCACAGTTA    3300

TATGTTCTCC TGCATCTGTA TCTAGCACTA CACAAGAAGT ATCCATTCCT GAATCTACTA    3360

CATACACCCC CGCACAGACC TCCACCCCTG TGTCCTCAAG CACCCAGGAA GACGCAGTGC    3420

AAACGCCGCC TAGAAAACGA GCACGAGGAG TCCAACAGTC ACCTTGCAAC GCCTTGTGTG    3480

TGGCCCACAT TGGACCCGTG GACAGTGGAA ACCACAACCT CATCACTAAC AATCACGACC    3540

AGCACCAAAG AAGGAACAAC AGTAACAGTT CAGCTACGCC TATAGTGCAA TTTCAAGGTG    3600

AATCTAATTG TTTAAAGTGT TTTAGATATA GGCTAAATGA CAAACACAGA CATTTATTTG    3660

ATTTAATATC ATCAACGTGG CACTGGGCCT CCCCAAAGGC ACCACATAAA CATGCCATTG    3720

TAACTGTAAC ATATCATAGT GAGGAACAAA GGCAACAGTT TTTAAATGTT GTAAAAATAC    3780

CACCTACTAT TAGGCACAAA CTGGGGTTTA TGTCACTGCA CCTATTGTAA TTTGTATATA    3840

TGTAAATGTG TAAATATATG GTATTGGTGT AATCAACTG TACATGTATG GAAGTGGTAC    3900

CTGTACAAAT AGCTGCAGGA ACAACCAGCA CATTAATACT GCCTGTTATA ATTGCATTTG    3960

TTGTATGTTT TGTTAGCATC ATACTTATTG TATGGATATC TGACTTTATT GTGTACACAT    4020

CTGTGCTAGT ACTAACACTG CTTTTATACT TACTATTGTG GCTGCTATTA CAACCCCCT    4080

TGCAATTTTT CCTACTAACT CTACTTGTGT GTTACTGTCC CGCATTGTAT ATACACCACT    4140

ACATTGTTAA CACACAGCAA TGATGCTAAC ATGTCAATTT AATGATGGAG ATACATGGCT    4200

GGGTTTGTGG TTGTTATGTG CCTTTATTGT AGGGGTGTTG GGGTTATTAT TAATGCACTA    4260

TAGAGCTGTA CAAGGCGATA AACACACCAA ATGTAACAAG TGTAACAAAC ACACCTGTAA    4320

TGCTGATTAT GTAACTATGC ATCATGATAC TGCTGGTGAT TATATATATA TGAATTAGAG    4380

TAAAACTTTT TTTATATTTG TAACAGTGTA TGTTTTGTAT ACCATGGCAC ATAGTAGGGC    4440

CCGACGACGC AAGCGTGCGT CAGCTACACA GCTATATCAA ACATGTAAAC TTACTGGAAC    4500

ATGCCCCCCA GATGTAATTC CTAAGGTGGA GCACAACACC ATTGCAGATC AAATATTAAA    4560

ATGGGGAAGT TTGGGGGTTT TTTTTGGAGG GTTGGGTATA GGCACCGGTT CCGGCACTGG    4620

GGGTCGTACT GGCTATGTTC CCTTAGGAAC TTCTGCAAAA CCTTCTATTA CTAGTGGGCC    4680

TATGGCTCGT CCTCCTGTGG TGGTGGAGCC TGTGGCCCCT TCGGATCCAT CCATTGTGTC    4740
```

```
TTTAATTGAA GAATCAGCAA TCATTAACGC AGGGGCGCCT GAAATTGTGC CCCCTGCACA      4800

CGGTGGGTTT ACAATTACAT CCTCTGAAAC AACTACCCCT GCAATATTGG ATGTATCAGT      4860

TACTAGTCAT ACTACTACTA GTATATTTAG AAATCCTGTC TTTACAGAAC CTTCTGTAAC      4920

ACAACCCCAA CCACCCGTGG AGGCTAATGG ACATATATTA ATTTCTGCAC CCACTATAAC      4980

GTCACACCCT ATAGAGGAAA TTCCTTTAGA TACTTTGTG ATATCCTCTA GTGATAGCGG       5040

TCCTACATCC AGTACCCCTG TTCCTGGTAC TGCACCTAGG CCTCGTGTGG GCCTATATAG      5100

TCGTGCATTG CACCAGGTGC AGGTTACAGA CCCTGCATTT CTTTCCACTC CTCAACGCTT      5160

AATTACATAT GATAACCCTG TATATGAAGG GGAGGATGTT AGTGTACAAT TTAGTCATGA      5220

TTCTATACAC AATGCACCTG ATGAGGCTTT TATGGACATA ATTCGTTTGC ACAGACCTGC      5280

TATTGCGTCC CGACGTGGCC TTGTGCGGTA CAGTCGCATT GGACAACGGG GGTCTATGCA      5340

CACTCGCAGC GGAAAGCACA TAGGGGCCCG CATTCATTAT TTTTATGATA TTTCACCTAT      5400

TGCACAAGCT GCAGAAGAAA TAGAAATGCA CCCTCTTGTG GCTGCACAGG ATGATACATT      5460

TGATATTTAT GCTGAATCTT TTGAACCTGA CATTAACCCT ACCCAACACC CTGTTACAAA      5520

TATATCAGAT ACATATTTAA CTTCCACACC TAATACAGTT ACACAACCGT GGGGTAACAC      5580

CACAGTTCCA TTGTCAATTC CTAATGACCT GTTTTTACAG TCTGGCCCTG ATATAACTTT      5640

TCCTACTGCA CCTATGGGAA CACCCTTTAG TCCTGTAACT CCTGCTTTAC CTACAGGCCC      5700

TGTTTTCATT ACAGGTTCTG GATTTTATTT GCATCCTGCA TGGTATTTTG CACGTAAACG      5760

CCGTAAACGT ATTCCCTTAT TTTTTTCAGA TGTGGCGGCC TAGCGACAGC ACAGTATATG      5820

TGCCTCCTCC TAACCCTGTA TCCAAAGTTG TTGCCACGGA TGCTTATGTT ACTCGCACCA      5880

ACATATTTTA TCATGCCAGC AGTTCTAGAC TTCTTGCAGT GGGTCATCCT TATTTTTCCA      5940

TAAAACGGGC TAACAAAACT GTTGTGCCAA AGGTGTCAGG ATATCAATAC AGAGTATTTA      6000

AGGTGGTGTT ACCAGATCCT AACAAATTTG CATTGCCTGA CTCGTCTCTT TTTGATCCCA      6060

CAACACAACG TTTGGTATGG GCATGCACAG GCCTAGAGGT GGGCCGGGGA CAGCCATTAG      6120

GTGTGGGTGT AAGTGGACAT CCTTTCCTAA ATAAATATGA TGATGTTGAA AATTCAGGGA      6180

GTGGTGGTAA CCCTGGACAG GATAACAGGG TTAATGTAGG TATGGATTAT AAACAAACAC      6240

AATTATGCAT GGTTGGATGT GCCCCCCCTT TGGGCGAGCA TTGGGGTAAA GGTAAACAGT      6300

GTACTAATAC ACCTGTACAG GCTGGTGACT GCCCGCCCTT AGAACTTATT ACCAGTGTTA      6360

TACAGGATGG CGATATGGTT GACACAGGCT TTGGTGCTAT GAATTTTGCT GATTTGCAGA      6420

CCAATAAATC AGATGTTCCT ATTGACATAT GTGGCACTAC ATGTAAATAT CCAGATTATT      6480

TACAAATGGC TGCAGACCCA TATGGTGATA GATTATTTTT TTTTCTACGG AAGGAACAAA      6540

TGTTTGCCAG ACATTTTTTT AACAGGGCTG GCGAGGTGGG GGAACCTGTG CCTGATACTC      6600

TTATAATTAA GGGTAGTGGA AATCGCACGT CTGTAGGGAG TAGTATATAT GTTAACACCC      6660

CAAGCGGCTC TTTGGTGTCC TCTGAGGCAC AATTGTTTAA TAAGCCATAT TGGCTACAAA      6720

AAGCCCAGGG ACATAACAAT GGTATTTGTT GGGGTAATCA ACTGTTTGTT ACTGTGGTAG      6780

ATACCACACG CAGTACCAAC ATGACATTAT GTGCATCCGT AACTACATCT TCCACATACA      6840

CCAATTCTGA TTATAAAGAG TACATGCGTC ATGTGGAAGA GTATGATTTA CAATTTATTT      6900

TTCAATTATG TAGCATTACA TTGTCTGCTG AAGTAATGGC CTATATTCAC ACAATGAATC      6960

CCTCTGTTTT GGAAGACTGG AACTTTGGGT TATCGCCTCC CCCAAATGGT ACATTAGAAG      7020

ATACCTATAG GTATGTGCAG TCACAGGCCA TTACCTGTCA AAAGCCCACT CCTGAAAAGG      7080

AAAAGCCAGA TCCCTATAAG AACCTTAGTT TTTGGGAGGT TAATTTAAAA GAAAAGTTTT      7140
```

```
                                    -continued

CTAGTGAATT  GGATCAGTAT  CCTTTGGGAC  GCAAGTTTTT  GTTACAAAGT  GGATATAGGG    7200

GACGGTCCTC  TATTCGTACC  GGTGTTAAGC  GCCCTGCTGT  TTCCAAAGCC  TCTGCTGCCC    7260

CTAAACGTAA  GCGCGCCAAA  ACTAAAAGGT  AATATATGTG  TATATGTACT  GTTATATATA    7320

TGTGTGTATG  TACTGTTATG  TATATGTGTG  TATGTACTGT  TATATGTATG  TGTGTTGTAT    7380

ATATGTGTGT  ATATATGTGT  ATGTGTGTAT  ATGTATATGT  ATGTGTTGTG  TATATATATG    7440

TGTGTGTGTG  TTATGTGTGT  AATGTAATTT  ATTTGTGTAA  TGTGTATGTG  TGTTTATGTG    7500

CAATAAACAA  TTAACTACAC  CCTGTGACTC  AGTGGCTGTT  GCACGCGTTT  TGGTTTGCAC    7560

GCGCCTTACA  CACATAAGTA  ATATACATGC  ACAATATATA  TATTTTTGTT  ACAATAATAT    7620

ATTTTTATAT  TTGCAACCGT  TTTCGGTTGC  CCTTGGCATA  CACTTTCCAC  CAATTTGTTA    7680

CAACGTGTTG  CCTGTTAATC  CTATATATTT  TGTGCCAGGT  ACACATTGCC  CTGCCAAGTT    7740

CATTGCCAAG  TGCATCATAT  CCTGCCAACC  ACACACCTGG  CGCCAGGGTG  CGGTATTGCC    7800

TTACTCATAT  GTTTATTGCC  ACTGCAATAA  ACCTGTCTTT  GTGTTATACT  TTTCTGCACT    7860

GTAGCCAACT  CTTAAAAGCA  TTTTTGGCTT  GTAGCAGAAC  ATTTTTTTGC  TCTTACTGTT    7920

TGGTATACAA  TAACATAAAA  ATGAGTAACC  TAAGGTCACA  CACCTGCAAC  CGGTTTCGGT    7980

TATCCACACC  CTACATATTT  CCTTCTTATA                                        8010
```